(12) United States Patent
Kahlman et al.

(10) Patent No.: US 11,534,130 B2
(45) Date of Patent: Dec. 27, 2022

(54) DEVICE, SYSTEM AND METHOD FOR DETECTING A CARDIAC AND/OR RESPIRATORY DISEASE OF A SUBJECT

(71) Applicant: KONINKLIJKE PHILIPS N.V., Eindhoven (NL)

(72) Inventors: Josephus Arnoldus Henricus Maria Kahlman, Tilburg (NL); Jan Valentin Wendelin Sebastian Werth, Eindhoven (NL); Rick Bezemer, Amsterdam (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 333 days.

(21) Appl. No.: 15/566,926

(22) PCT Filed: Apr. 15, 2016

(86) PCT No.: PCT/EP2016/058395
§ 371 (c)(1),
(2) Date: Oct. 16, 2017

(87) PCT Pub. No.: WO2016/166318
PCT Pub. Date: Oct. 20, 2016

(65) Prior Publication Data
US 2018/0125444 A1    May 10, 2018

(30) Foreign Application Priority Data

Apr. 16, 2015   (EP) ..................................... 15163872

(51) Int. Cl.
*A61B 7/00*     (2006.01)
*A61B 5/00*     (2006.01)
(Continued)

(52) U.S. Cl.
CPC ................ *A61B 7/003* (2013.01); *A61B 5/08* (2013.01); *A61B 5/1135* (2013.01);
(Continued)

(58) Field of Classification Search
CPC ........... A61B 7/003; A61B 7/00; A61B 7/005; A61B 7/04; A61B 5/08; A61B 5/1135;
(Continued)

(56) References Cited

U.S. PATENT DOCUMENTS 6,527,729 B1    3/2003  Turcott
2007/0293781 A1* 12/2007  Sims .................... A61B 5/1135
                                                    600/534

(Continued)

FOREIGN PATENT DOCUMENTS

| JP | 2005066045 A | 3/2005 |
| JP | 2013123495 A | 6/2013 |
| WO | 2009054549 A1 | 4/2009 |

OTHER PUBLICATIONS

English translation of JP2013123495, Sharp (Year: 2013).*

*Primary Examiner* — Tse W Chen
*Assistant Examiner* — Avery M Foley

(57) ABSTRACT

The present invention relates to device, system and method for detecting a cardiac and/or respiratory disease of a subject. The proposed device comprises a sound input (20) for obtaining a sound signal representing sounds generated by the subject's body; a motion input (21) for obtaining a motion signal representing motions generated by the subject's body; and a processor (22) for processing the obtained sound signal and motion signal. This processing includes identifying inhalation and/or exhalation periods of the subject based on the motion signal, detecting abnormal lung sounds during inhalation and/or exhalation periods based on the sound signal, determining abnormal lung sound characteristics of the detected abnormal lung sounds, determining breathing characteristics of the subject's breathing based on the sound signal, determining the phase of the abnormal lung sounds in the inhalation-exhalation cycle, and detecting a cardiac and/or respiratory disease of the subject based on the (Continued)

determined abnormal lung sound characteristics, the determined breathing characteristics and the determined phase of the abnormal lung sounds in the inhalation-exhalation cycle.

15 Claims, 2 Drawing Sheets

(51) Int. Cl.
    *A61B 5/113*       (2006.01)
    *A61B 5/08*        (2006.01)
    *A61B 5/0205*     (2006.01)

(52) U.S. Cl.
    CPC .......... *A61B 5/6833* (2013.01); *A61B 5/0205* (2013.01); *A61B 5/4842* (2013.01); *A61B 5/6831* (2013.01)

(58) Field of Classification Search
    CPC ... A61B 5/6833; A61B 5/0205; A61B 5/4842; A61B 5/6831; A61B 5/0803; A61B 5/0816; A61B 8/00
    See application file for complete search history.

(56) References Cited

U.S. PATENT DOCUMENTS

| | | | |
|---|---|---|---|
| 2008/0190430 A1* | 8/2008 | Melker | A61B 5/08 128/204.23 |
| 2010/0179438 A1 | 7/2010 | Heneghan et al. | |
| 2011/0125044 A1 | 5/2011 | Rhee et al. | |
| 2012/0041279 A1 | 2/2012 | Freeman et al. | |
| 2013/0030257 A1* | 1/2013 | Nakata | G01S 7/003 600/301 |
| 2013/0060100 A1 | 3/2013 | Wurm et al. | |
| 2013/0237862 A1* | 9/2013 | Song | A61B 7/00 600/483 |
| 2013/0281874 A1 | 10/2013 | Nishida | |
| 2013/0310657 A1 | 11/2013 | Sullivan | |

* cited by examiner

DEVICE, SYSTEM AND METHOD FOR DETECTING A CARDIAC AND/OR RESPIRATORY DISEASE OF A SUBJECT

This application is the U.S. National Phase application under 35 U.S.C. § 371 of International Application No. PCT/EP2016/058395, filed on Apr. 15, 2016, which claims the benefit of European Application No. 15163872.3, filed Apr. 16, 2015. These applications are hereby incorporated by reference herein.

FIELD OF THE INVENTION

The present invention relates to a device, system and method for detecting a cardiac and/or respiratory disease of a subject, such as pneumonia, pulmonary edema and/or heart failure.

BACKGROUND OF THE INVENTION

In many clinical scenarios, such as in home care, in- and out-of hospital emergency care, and in screening/triage settings (e.g. in Africa, India, and Brazil), it is desired to have a unobtrusive quick and reliable spot check of a subject's medical condition on basis of vital parameters.

The Atlas device, a multi-parameter patient monitoring device distributed e.g. by Welch Allyn, and described in J. Schmidt, "Summary for FDA approval," Philips, Boeblingen, Germany, 2014 (currently available at http://www.accessdata.fda.gov/cdrh_docs/pdf13/K132320.pdf) is a single sensor modality able to unobtrusively measure respiratory rate, pulse rate, posture, activity level and activity classification, based on accelerometers fitted in a small box mechanically attached to the human body. The foreseen application in the general ward is to detect patient deterioration. For the Africa use-scenario the Atlas device is optimized for pneumonia diagnosis by detecting a fast- and shallow breathing rate, but the specificity is limited as many non-pulmonary conditions could lead to elevated breathing rate (e.g. dehydration, anemia, and fever).

A more specific (and more classical) way of diagnosing a lot of different cardiac and pulmonary diseases is done by auscultation. Auscultation is the use of a stethoscope to listen to the different body sounds. Different diseases have different sound profiles. A well trained doctor can identify and also rank the severity of the disease by listening to the body sounds. For example, the detection of crackling sounds during inhalation, which is strongly linked to water accumulation in the lungs as a result of, for example, inflammation (e.g. pneumonia), heart failure, hypertension, intravenous fluid therapy-associated fluid overload (e.g. in the ER, OR, and ICU). As another example, a third heart sound (S3), which is a rare extra heart sound that occurs soon after the normal two "lub-dub" heart sounds (S1 and S2), is associated with heart failure.

US 2012/041279 A1 discloses devices and methods for assessing a patient. The devices have at least one impedance measuring element functionally connected to a programmable element, programmed to analyze an impedance measurement, and to provide an assessment of at least one respiratory parameter of the patient. In one embodiment, measurements of respiratory motion derived from a technology including impedance plethysmography, accelerometers placed on the body, video images, acoustic signals or other means of tracking motion of the thorax, abdomen or other body parts is calibrated or correlated with another technology that assesses respiratory status.

US 2013/0060100 A1 discloses a device and method for monitoring and analyzing breathing sounds, the device including at least one microphone adapted and configured for placement adjacent a body to be monitored for contactless recording of breathing sounds, a motion detector using an ultrasound distance sensor to detect the patient body motions, and a processor coupled to the microphones and the motion detector for receiving and processing the breathing sounds and patient motions to detect abnormal breathing events.

There are large opportunities to extend the application of the Atlas device towards lower acuity care settings like Hospital-to-Home, Connected Primary and Secondary Care, and Home Respiratory Care. There is a need to improve specificity and accuracy.

SUMMARY OF THE INVENTION

It is an object of the present invention to provide a device, system and method for detecting a cardiac and/or respiratory disease of a subject with improved specificity and accuracy.

In a first aspect of the present invention a device for detecting a cardiac and/or respiratory disease of a subject is presented comprising
  a sound input for obtaining a sound signal representing sounds generated by the subject's body;
  a motion input for obtaining a motion signal representing motions generated by the subject's body; and
  a processor for processing the obtained sound signal and motion signal by
  identifying inhalation and/or exhalation periods of the subject based on the motion signal,
  detecting abnormal lung sounds during inhalation and/or exhalation periods based on the sound signal,
  determining abnormal lung sound characteristics of the detected abnormal lung sounds,
  determining breathing characteristics of the subject's breathing based on the sound signal,
  determining the phase of the abnormal lung sounds in the inhalation-exhalation cycle, and
  detecting a cardiac and/or respiratory disease of the subject based on the determined abnormal lung sound characteristics, the determined breathing characteristics and the determined phase of the abnormal lung sounds in the inhalation-exhalation cycle.

In a further aspect of the present invention a system for detecting a cardiac and/or respiratory disease of a subject is presented comprising
  a sound sensor for sensing sounds generated by the subject's body and generating a sound signal representing the sensed sounds;
  a motion sensor for sensing motions generated by the subject's body and generating a motion signal representing the sensed motions;
  coupling means for acoustically coupling the sound sensor to the subject's body and for mechanically coupling the motion sensor to the subject's body; and
  a device as claimed in claim 1 for detecting a cardiac and/or respiratory disease of the subject based on obtained sound signal and motion signal.

In a further aspect of the present invention a method for determining information for use in detecting a cardiac and/or respiratory disease of a subject is presented comprising
  obtaining a sound signal representing sounds generated by the subject's body;
  obtaining a motion signal representing motions generated by the subject's body;

identifying inhalation and/or exhalation periods of the subject based on the motion signal;

detecting abnormal lung sounds during inhalation and/or exhalation periods based on the sound signal;

determining abnormal lung sound characteristics of the detected abnormal lung sounds;

determining breathing characteristics of the subject's breathing based on the sound signal;

determining the phase of the abnormal lung sounds in the inhalation-exhalation cycle; and issuing the determined abnormal lung sound characteristics, the determined breathing characteristics and the determined phase of the abnormal lung sounds in the inhalation-exhalation cycle for use in detecting a cardiac and/or respiratory disease of the subject based thereon.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed system, method, processor, computer program and medium have similar and/or identical preferred embodiments as the claimed device and as defined in the dependent claims.

While cardiac and lung sounds provide superior specificity over simply heart and breathing rate, the automated analysis of these sounds requires information of the phase with the cardiac and respiratory cycle (also called inhalation-exhalation cycle or breathing cycle hereinafter). This, however, is sometimes very difficult to derive from the sounds only, which hampers automated analysis. Therefore, synchronized accelerometer signals are used according to the present invention to monitor the inhalation-exhalation cycle and provide a measure of a breathing characteristic, in particular the breathing depth.

The motion signal may represent and may be used to derive local body accelerations, local body velocity, local body positions/angles and body (e.g. cardiac and/or respiratory) sounds. The sound signal may represent and may be used to derive abnormal lung sounds and abnormal lung sound characteristics, e.g. the number of abnormal lung sounds, during inhalation and/or exhalation, which has been detected by use of the motion signals. Based thereon the desired cardiac and/or respiratory disease of the subject is determined.

It shall be noted that the expression "abnormal lung sound" shall be understood generally in the sense of "specific or adventitious lung (or breath) sound", which are related to a certain lung or respiratory disease. Such abnormal lung sounds are specifically crackles for pneumonia and congestive heart failure (CHF), but may be other lung sounds, such as wheeze, rhonchi, stridor, inspiratory gasp, pleural friction rub, or Hamman's sign for the same and/or other lung or respiratory diseases.

Embodiments are herein described with particular reference to "crackles" as one example of "abnormal lung sounds". However, each time when particular reference is made to crackle(s) herein, this shall generally be understood broadly as a reference to one or more "abnormal lung sound(s)", i.e. the respective examples and embodiments may generally be used in connection with one or more other abnormal lung sounds than crackles as well.

Hence, the proposed system comprises a combination of a motion sensor and a sound sensor (acoustic sensor) which enables (1) to enhance the specificity of respiratory disease diagnosing (e.g. pneumonia detection), (2) to enable monitoring of the progression of abnormal lung sound-specific diseases (in e.g. a hospital to home application), and (3) to improve the accuracy of respiration and pulse rate monitoring outcome. By the combination of said two sensing modalities the outcome is improved because classification is more accurate. Even the existing accelerometer-based respiration rate and pulse rate measurement can be made more accurate and artifact robust when adding sound signals (acoustic signals).

An application of the present invention is the improvement of the Atlas-based pneumonia detection. Currently, the assessment is solely based on breathing rate assessment. However, the specificity of this method is very low as many non-pulmonary conditions like dehydration, anemia, and fever, are known to also lead to elevated breathing rates. The presence of crackles in the lung sounds during inhalation and/or exhalation, in contrast, is a very specific marker of pneumonia (especially considering the target population). The amount of abnormal lung sounds is proportional to the degree of the disease normalized to the breathing volume. Hence, combining the sensed sounds with the sensed motion will allow the normalization to breathing depth/volume.

Further, the present invention allows trending, for which purpose the sensors should be kept at the same spot using e.g. a patch.

In an embodiment from the measurements of said sensors a heart rate (variability), arrhythmias, breathing rate, relative breathing depth, and cardiac and respiratory sound properties (e.g. the presence of third heart sound or the presence of abnormal lung sounds, respectively) may be additionally derived, which may be used in addition for detecting a cardiac and/or respiratory disease. The physiological condition may be a cardiac status (e.g. heart failure) or a respiratory status (e.g. pneumonia).

In a preferred embodiment the processor is configured to determine the count, amplitude and/or frequency of the detected abnormal lung sounds as abnormal lung sound characteristics. This information further helps in the detection of the cardiac and/or respiratory disease.

In another embodiment the processor is configured to determine the breathing depth and/or breathing rate of the subject's breathing as breathing characteristics. This information as well further helps in the detection of the cardiac and/or respiratory disease.

In a preferred embodiment the processor is configured to determine the count of the detected abnormal lung sounds as abnormal lung sound characteristic, to determine the breathing depth of the subject's breathing as breathing characteristic, to normalize the determined abnormal lung sound count based on the determined breathing depth and to determine a degree of disease proportional to the amount of normalized abnormal lung sound count. Thus, in order to properly interpret and monitor the disease progression over time, normalization on basis of the breathing depth (as breathing characteristic) is preferred in this embodiment. Furthermore, the degree (e.g. count, frequency, amplitude) of present lung sound abnormalities may be normalized to the relative breathing depth.

In another embodiment the abnormal lung sound group distribution and length may be determined and evaluated. The disease is generally correlated to a factor of length and count of abnormal lung sound groups, which may, however, be the same as numbers of abnormal lung sounds. The more abnormal lung sounds, the longer or more abnormal lung sound groups can be found.

According to the invention the phase of the abnormal lung sounds in the inhalation-exhalation cycle (as determined from the detected inhalation and exhalation periods) is determined and additionally evaluated. Particularly the location and timing of the abnormal lung sounds in the breathing cycle may be determined and evaluated. In certain diseases (e.g. pneumonia) the timing of crackles can give information on the severity. A pneumonia for example is quite severe if the crackle appears also in the inhaling phase and not only during exhaling.

An accelerometer may be used as motion sensor to sense movements of particular body locations that are indicative to the breathing depth and are used to improve the accuracy of a spot-measurement, in particular by normalization to breathing depth, standardization of breathing depth, averaging of breathing cycles, and to allow trending of disease progression over time.

In another embodiment the processor is configured to determine cardiac characteristics based on the sound signal and/or motion signal and to use the determined cardiac characteristics in the detection of a cardiac and/or respiratory disease of the subject. Preferably, the heart rate, heart rate variability and/or a third heart sound are determined as cardiac characteristics. This information may further improve the detection of the cardiac and/or respiratory disease.

It may further be foreseen that the processor is configured to determine artifact sounds, in particular coughing, laughing, talking, snoring and/or crying, based on the sound signal and/or the motion signal and to take the artifact sound into account in the detection of a cardiac and/or respiratory disease of the subject.

The present invention is preferably used to detect one or more of pneumonia, pulmonary edema and heart failure and/or to monitor the disease progression over time.

The present invention can be implemented as a dedicated pocket-sized stand-alone device or as a software application in existing smartphones, which may already comprise accelerometers, microphones, and the option to connect a (dedicated) electronic stethoscope.

The sound sensor may comprise a microphone, an air pressure sensor, an accelerometer and/or a gyroscope and the motion sensor may comprise an accelerometer, a gyroscope and/or a magnetometer.

Preferably said sound sensor and said motion sensor are arranged in one or more patches configured for being attached to the subject's skin.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
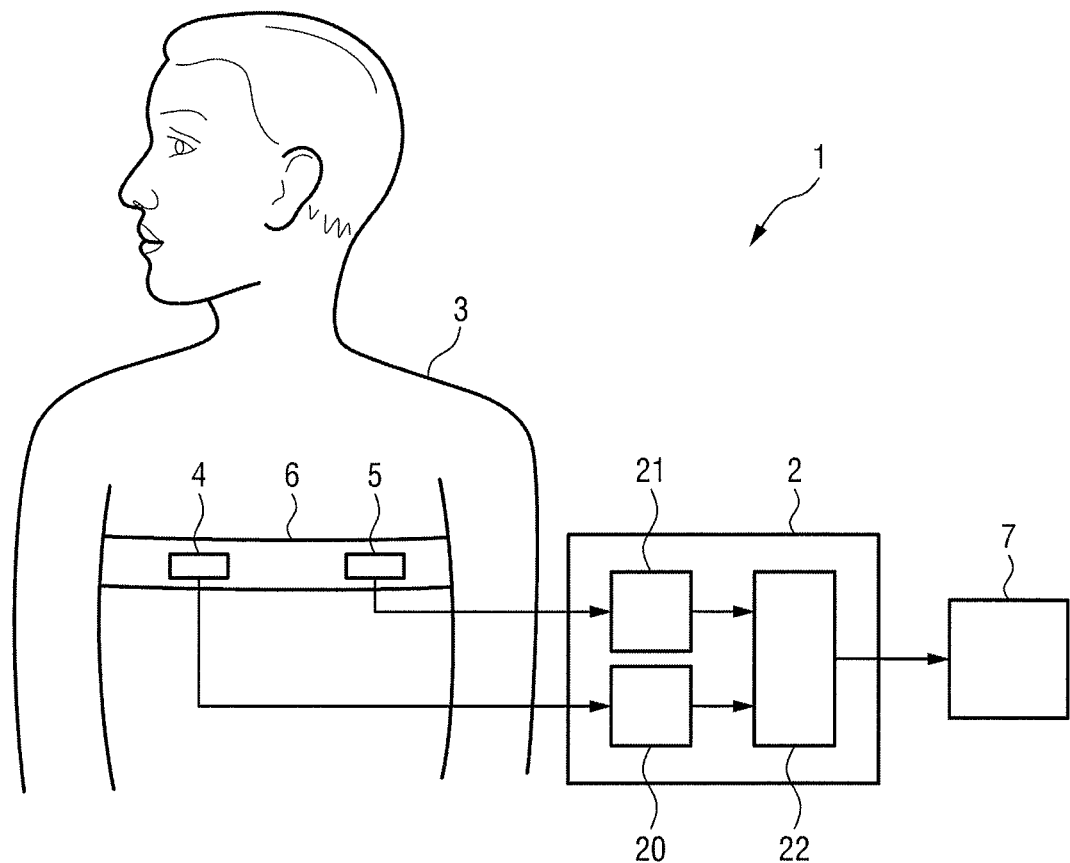
FIG. 1 shows a schematic diagram of a first embodiment of a system and a device according to the present invention.

FIG. 1 shows a schematic diagram of a first embodiment of a system 1 and a device 2 according to the present invention for detecting a cardiac and/or respiratory disease of a subject 3. The system 1 comprises a sound sensor 4 for sensing sounds generated by the subject's body and generating a sound signal representing the sensed sounds. The sound sensor 4 may e.g. be a microphone that is acoustically coupled to the subject's body, e.g. the subject's chest. The system 1 further comprises a motion sensor 5 for sensing motions generated by the subject's body and generating a motion signal representing the sensed motions. The motion sensor 5 may e.g. be an accelerometer that is mechanically coupled to the subject's body, e.g. the subject's chest or belly area.

For coupling the sound sensor 4 and the motion sensor 5 to the respective portion of the subject's body the system 1 comprises coupling means 6. Said coupling means 6 may be a belt that holds the sensors 4, 5, or a self-adhesive pad that holds the sensors 4, 5, or an adhesive arranged on the bottom side of the sensors 4, 5 for adhering them to the subject's skin. The sensors 4, 5 may also be combined into a sound package that is attached to the subject's body.

The sound signal and the motion signal acquired by the sound sensor 4 and the motion sensor 5 the system 1 may be transferred in a wired or wireless manner to the device 2, e.g. by use of a common interface or separate interfaces for data transfer. Finally, the system 1 comprises the device 2 for detecting a cardiac and/or respiratory disease of the subject based on obtained sound signal and motion signal.

The device 2 is in this embodiment a separate device which is coupled with the sensors 4, 5 in a wired or wireless manner. For instance, via a network, such as a Wifi network, a LAN network, a communications network, or via any other way such as Bluetooth, the signals are retrieved by the device 2 from the sensors 4, 5 or are actively transmitted by the sensors 4, 5. For obtaining the signals the device 2 comprises a sound input 20 for obtaining a sound signal representing sounds generated by the subject's body and a motion input 21 for obtaining a motion signal representing motions generated by the subject's body.

Further, the device 2 comprises a processor 22 for processing the obtained sound signal and motion signal. In said processing inhalation and/or exhalation periods of the subject are identified based on the motion signal. Further, crackles (and/or other lung sounds; only crackles will be used for explanation in the following) are detected during inhalation and/or exhalation periods based on the sound signal. From the detected crackles crackle characteristics are determined, such as a crackle count indicating the number of crackles. From the sound signal breathing characteristics of the subject's breathing are detected. Still further, the phase of the abnormal lung sounds in the inhalation-exhalation cycle is determined. Finally, a cardiac and/or respiratory disease of the subject is detected based on the determined crackle characteristics, the determined breathing characteristics and the determined phase of the abnormal lung sounds in the inhalation-exhalation cycle.

An information about the result of the detection may be issued, e.g. to an external output device 7, which may be doctor's device (e.g. PC, workstation, smartphone, tablet, etc. of the doctor), the central monitor for monitoring patients in a station of a hospital, or a device of the subject 3 (e.g. PC, workstation, smartphone, tablet, etc. of the subject 3). The output device may also be integrated into the device 2, e.g. in the form of a user interface such as a monitor or display.

Figure 2:
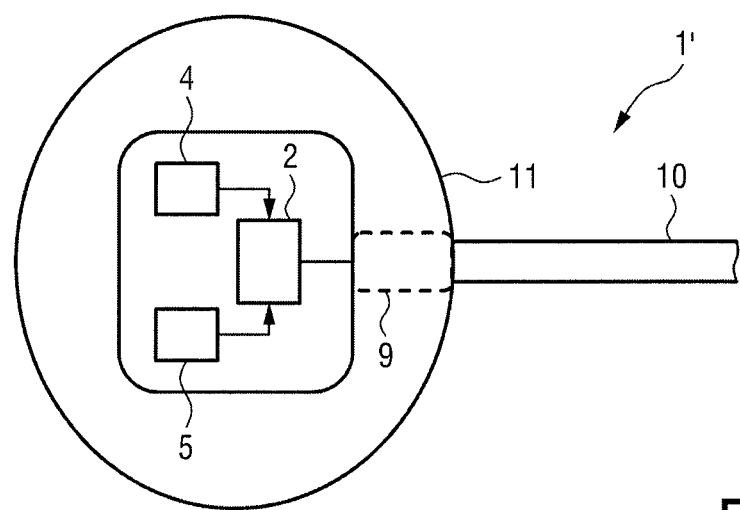
FIG. 2 shows a schematic diagram of a second embodiment of a system according to the present invention.

FIG. 2 shows a schematic diagram of a second embodiment of a system 1' according to the present invention. In this embodiment the system 1' comprises a package 8 that may be attached to the chest or back of the subject. The package 8 may include the sensors 4, 5 and the device 2. Hence, the sensed signals are directly processed in the package 8. Additionally, an interface 9 may be provided for outputting the sensed signals and/or the result of the detection performed by the device 2 via a cable 10 (or, alternatively, via a wireless connection). The package 8 is preferably mounted on a pad 11, which may have an adhesive layer on the bottom side so that it can be adhered to the subject's skin.

The combination of motion and sound signals is preferably acquired simultaneously and may be used to diagnose and/or monitor cardiac or respiratory disease (e.g. heart failure or pneumonia) by integrative interpretation of abnormalities in the heart and breathing rates (i.e. too high or too low) and sounds (e.g. a third heart sound in addition to crackling in the lung sounds).

A preferred application of the present invention is an improvement of the Atlas-based respiratory disease detection. The presence of crackles in the lung sounds during inhalation and/or exhalation has been found to be a very specific marker of two of the most common respiratory conditions: pneumonia and pulmonary edema. Pneumonia is the number one cause of death in children under the age of five in Africa and Asia and pulmonary edema is a highly common complication of heart failure and intravenous fluid therapy-associated fluid overload.

For all these conditions, the amount of crackles is proportional to the degree of the condition and the breath volume. Hence, in order to properly interpret and monitor the progression of the condition over time, normalization on basis of the breathing depth is preferably applied. This may be done using the motion sensor. Movements of particular body locations (e.g. the chest wall or the belly portion) are indicative to the breathing depth and may be used to (1) improve the accuracy of a spot-measurement of breathing rate and allow (2) crackle count normalization to (relative) breathing depth; (3) averaging of breathing cycles; (4) trending of disease progression over time; and (5) protocolled standardization of breathing depth (e.g. a minimum relative breathing depth for adults).

For motion sensors, such as accelerometers, to provide an absolute value of the breathing depth, proper patient- and location-specific calibration may be advantageous. However, even without calibration, the motion signals can be beneficially applied to improve accuracy by averaging the crackle characteristics of distinct respiratory cycles and to compare relative (i.e. un-calibrated) breathing depths (which requires consistent placement amongst different subjects). Further, comparing distinct spot-checks (e.g. to determine a trend) requires always the same measuring conditions in terms of sensor position and subject posture.

Figure 3:
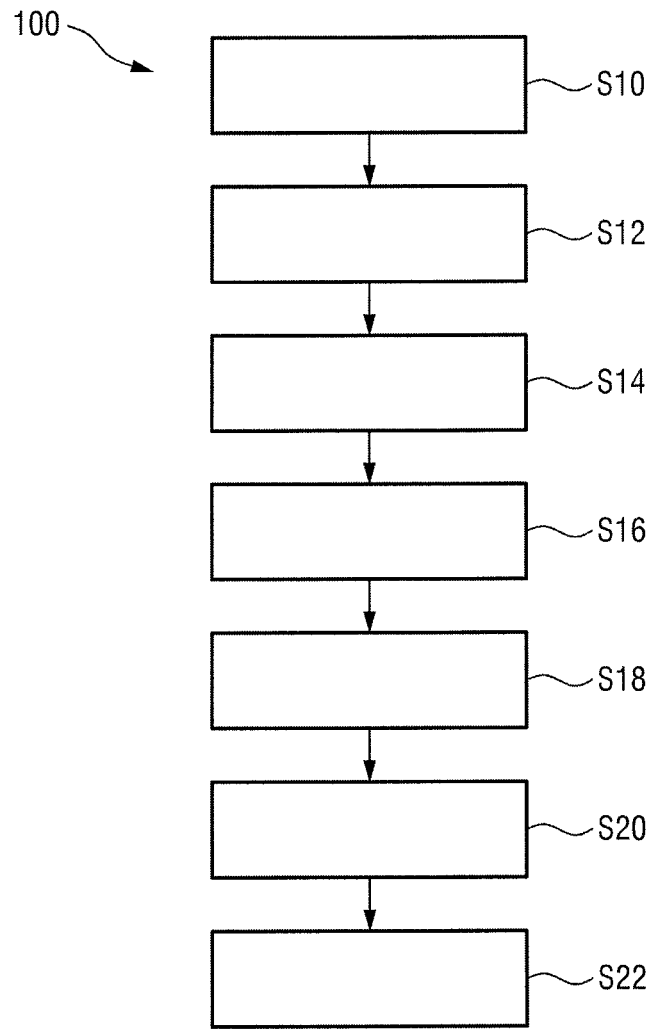
FIG. 3 shows a flowchart of a method for detecting a cardiac and/or respiratory disease of a subject according to the present invention.

A flowchart of a method 100 for detecting a cardiac and/or respiratory disease of a subject according to the present invention is shown in FIG. 3. The method 100 comprises the following steps:

S10: obtaining a sound signal representing sounds generated by the subject's body;

S12: obtaining a motion signal representing motions generated by the subject's body;

S14: identifying inhalation and/or exhalation periods of the subject based on the motion signal;

S16: detecting abnormal lung sounds during inhalation and/or exhalation periods based on the sound signal;

S18: determining abnormal lung sound characteristics of the detected abnormal lung sounds;

S20: determining breathing characteristics of the subject's breathing based on the sound signal and determining the phase of the abnormal lung sounds in the inhalation-exhalation cycle; and S22: detecting a cardiac and/or respiratory disease of the subject based on the determined abnormal lung sound characteristics, the determined breathing characteristics and the determined phase of the abnormal lung sounds in the inhalation-exhalation cycle.

Figure 4:
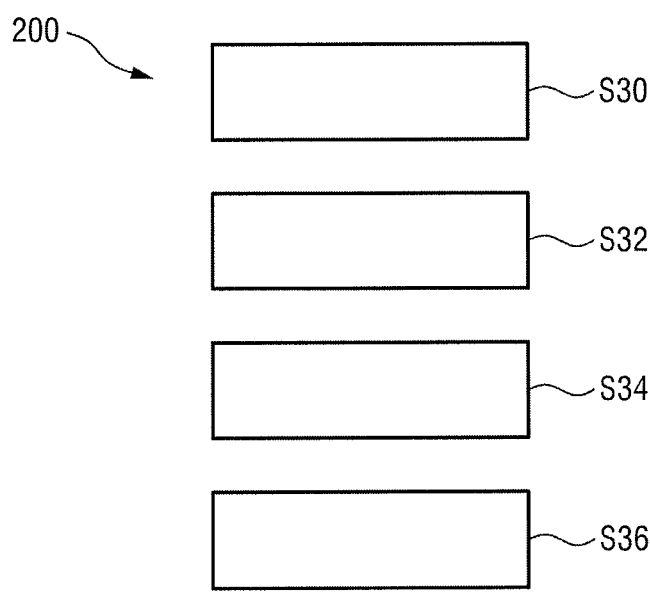
FIG. 4 shows a flowchart of an embodiment of a method for crackle detection according to the present invention.

FIG. 4 shows a flowchart of an embodiment of a method 200 for crackle detection according to the present invention. In a first step S30 one or more dedicated algorithms are applied to the sound signals for crackle identification (e.g. using classification via wavelet analysis (as e.g. described in A. Kandaswamy, C. Sathish Kumar, R. P. Ramanathan, S. Jayaraman and N. Malmurugan, "Neural classification of lung sounds using wavelet coefficients," Computers in Biology and Medicine, pp. 523-537, 2004) or several machine learning methods (as e.g. described in K. Sundaraj, R. Palaniappan, N. U. Ahamed, A. Sundaraj and S. Sundaraj, "Computer based respiratory sound analysis: a systematic review," IETE Technical Review, vol. 30, no. 3, pp. 248-256, 2013)). In a second step S32 crackle characteristics (e.g. count, timing and/or amplitudes) are determined in relation to the point in time during a respiratory cycle. In a third step S34 crackle characteristics are normalized by using the obtained accelerometer signals as an approximation for the airflow and volume. In a fourth step S36 the crackle characteristics are characterized, in combination with the breathing rate and/or (relative) depth information obtained from the motion signals, to diagnose pneumonia.

In another embodiment coughing, talking and crying may be detected as well from the sound signal and/or the motion signal and may contribute to the accuracy of the diagnosis.

In practical implementations of the proposed system, a dedicated patch, e.g. as shown in FIG. 2, comprises the combination of motion sensor(s) and sound sensor(s), whether or not located at different positions on the body and connected galvanically via e.g. flexible foil or wirelessly to the processor 22, which may also be a central processing unit. Motion may be measured by accelerometer(s), gyroscope(s) or magnetometer(s). Sound signals may be measured by microphone(s), accelerometer(s) or gyroscope(s). Multiple motion sensor and/or multiple sound sensors may be applied to achieve a directional effect or acoustic echo-canceling etc. Such a dedicated patch has the advantage that it maintains the same sensor location over time. This allows trending, which is a very important aspect of lung monitoring.

In another embodiment of the system all elements may be integrated into a portable electronic user device, such as a smartphone. Some existing smartphones comprise already a motion sensor and a sound sensor. Thus, the processor of the smartphone may just be programmed accordingly, e.g. by use of an application program ("app") to enable the smartphone to carry out the method of the present invention. The network functionality of the smartphone may be used to communicate with e.g. the hospital network, an external output device or another health-network. Other portable electronic user devices, such as smartphones or cameras, that may be worn by the subject in his pocket, e.g. of a jacket, that do not yet have a motion sensor and/or a sound sensor may be equipped accordingly to be able to carry out the method of the present invention. Such portable electronic user devices then represent embodiments of the proposed system.

Generally, different embodiments of the proposed system and device may be implemented on basis of their clinical application. The sensors may e.g. be embedded in a single small patch, but also in e.g. an larger I- or L-shaped patch which holds the motion sensor on the location of the Atlas device (at the lower left rib) and the sound sensor(s) higher on the chest.

Value segment solutions and connected primary and secondary care are directed to improve the Africa and Asia use-case for pneumonia detection. Because the cost of the device is a prime concern, the motion and the sound functionality may be combined in one single sensor, such as a high bandwidth accelerometer/gyroscope or a low frequency microphone comprising a heavy membrane, e.g. an (almost) DC coupled condenser or electret microphone, air pressure sensor, crystal microphone, etc.

For Hospital-to-Home and home healthcare a hand-held device may be designed, which can be used by a general practitioner, nurse, doctor, or non-medical (but preferably trained) personnel like home caregivers and community healthcare workers, for the diagnosis or follow-up (which preferably requires consistent placement and posture) of, for example, pneumonia, heart failure, and COPD patients.

The present invention may also be embedded in a wearable patch that can be work hospital-to-home for, for example, pneumonia, heart failure, and COPD patients. A wearable patch ensures that regular spot-check measurements are always performed at the same body-location. Performing the measurements in the same posture, and basic knowledge about the patient (e.g. age, height and weight), the motion signals provide a stable approximation for the air flow and volume, and can be reliably used for normalization of the lung sound analysis results. This enables valid trending of the disease progression or healing process.

The combination of motion (accelerometer, gyroscope) and sound signals acquired simultaneously with a sensor package attached to the chest or back can also be used to improve the reliability of fall detection.

For patient monitoring the present invention may also be embedded in a bedside monitor for patients in the emergency department, intensive care unit and operating room, to monitor the presence and extent of pulmonary edema, which is a common complication in patients receiving intravenous fluids (fluid overload). This works for both spontaneously breathing as well as for mechanically ventilated patients, e.g. to guide the weaning process in the ICU.

For home respiratory care the sleep quality is of strong interest in the biomedical imaging unit. The appearance and characteristics (e.g. rate, duration, intensity and nature) of sleep apnea, snoring, and coughing and activity during sleep is important clinical information to gather. The combination of motion sensor(s) and sound sensor(s) attached to the body can thus additionally be used to gather this information in a highly consistent and accurate way. This can be used, for example, to optimize the ventilation therapy (type of ventilator and mask, ventilator settings) and improve sleep position and comfort.

The idea of body sound analysis combined with motion sensing can further be used in additional use scenarios like pre-operative training of surgery patients (e.g. to practice abdominal breathing), alarming (improved fall detection), breath-support training for musicians and singers. When a microphone is present to pick up environmental sounds, even more applications in the field of smart-alarming, bed-leave detection, fall detection, nightmare detection etc. are feasible.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for detecting a cardiac and/or respiratory disease of a subject, comprising:
   a sound input for obtaining a sound signal representing sounds generated by the subject's body;
   a motion input for obtaining a motion signal representing breathing motions generated by the subject's body; and
   a processor for processing the obtained sound signal and motion signal by:
   identifying inhalation and/or exhalation periods of the subject based on the motion signal, wherein the inhalation and/or exhalation periods determine an inhalation-exhalation cycle,
   detecting abnormal lung sounds during the inhalation and/or exhalation periods based on the sound signal,
   determining abnormal lung sound characteristics of the detected abnormal lung sounds,
   determining breathing characteristics of the subject's breathing based on the sound signal,
   determining a phase for each of the abnormal lung sounds in the inhalation-exhalation cycle, the phase representing the timing of the abnormal lung sounds in the inhalation-exhalation cycle and the location of the abnormal lung sounds in the inhalation-exhalation cycle, and
   detecting a cardiac and/or respiratory disease of the subject based on the determined abnormal lung sound characteristics, the determined breathing characteristics and the determined phase of the abnormal lung sounds in the inhalation-exhalation cycle.

2. The device as claimed in claim 1, wherein the processor is configured to normalize the determined abnormal lung sound characteristics based on the motion signal and to use the normalized abnormal lung sound characteristics in the detection of the cardiac and/or respiratory disease of the subject.

3. The device as claimed in claim 2, wherein the processor is configured to determine a count of the detected abnormal lung sounds as abnormal lung sound characteristic, to determine a breathing depth of the subject's breathing as breathing characteristic, to normalize the determined abnormal lung sound count based on the determined breathing depth and to determine a degree of severity of disease proportional to the amount of normalized abnormal lung sound count.

4. The device as claimed in claim 1, wherein the processor is configured to determine a count, amplitude and/or frequency of the detected abnormal lung sounds as abnormal lung sound characteristics.

5. The device as claimed in claim 1, wherein the processor is configured to determine a breathing depth and/or breathing rate of the subject's breathing as breathing characteristics.

6. The device as claimed in claim 1, wherein the processor is configured to determine cardiac characteristics based on the sound signal and/or motion signal and to use the determined cardiac characteristics in the detection of the cardiac and/or respiratory disease of the subject.

7. The device as claimed in claim 6, wherein the processor is configured to determine a heart rate, heart rate variability and/or a third heart sound as cardiac characteristics.

8. The device as claimed in claim 1, wherein the processor is configured to determine artifact sounds, in particular coughing, laughing, talking, snoring and/or crying, based on the sound signal and/or the motion signal and to take one or more of the artifact sounds into account in the detection of a cardiac and/or respiratory disease of the subject.

9. The device as claimed in claim 1, wherein the cardiac and/or respiratory disease is one or more of pneumonia, pulmonary edema and heart failure.

10. The device as claimed in claim 1, wherein the processor is configured to monitor the disease progression over time.

11. A system for detecting a cardiac and/or respiratory disease of a subject, comprising:
- a sound sensor for sensing sounds generated by the subject's body and generating a sound signal representing the sensed sounds;
- a motion sensor for sensing motions generated by the subject's body and generating a motion signal representing the sensed motions;
- coupling means for acoustically coupling the sound sensor to the subject's body and for mechanically coupling the motion sensor to the subject's body; and
- a device as claimed in claim 1 for detecting the cardiac and/or respiratory disease of the subject based on obtained sound signal and motion signal.

12. The system as claimed in claim 11, wherein said sound sensor comprises a microphone, an air pressure sensor, an accelerometer and/or a gyroscope and said motion sensor comprises an accelerometer, a gyroscope and/or a magnetometer.

13. The system as claimed in claim 11, wherein said sound sensor and said motion sensor are arranged in one or more patches configured for being attached to the subject's skin.

14. A method for determining information for use in detecting a cardiac and/or respiratory disease of a subject, comprising:
- obtaining a sound signal representing sounds generated by the subject's body;
- obtaining a motion signal representing breathing motions generated by the subject's body;
- identifying inhalation and/or exhalation periods of the subject based on the motion signal, wherein the inhalation and/or exhalation periods determine an inhalation-exhalation cycle;
- detecting abnormal lung sounds during the inhalation and/or exhalation periods based on the sound signal;
- determining a count of the abnormal lung sounds;
- determining abnormal lung sound characteristics of the detected abnormal lung sounds;
- determining breathing characteristics of the subject's breathing based on the sound signal;
- determining a phase for each of the abnormal lung sounds in the inhalation-exhalation cycle, the phase representing the location and the timing of the abnormal lung sounds in the inhalation-exhalation cycle; and
- issuing the determined abnormal lung sound characteristics, the determined breathing characteristics and the determined phase of the abnormal lung sounds in the inhalation-exhalation cycle for use in detecting the cardiac and/or respiratory disease of the subject based thereon;
- wherein the count of abnormal lung sounds is indicative of a degree of severity of the cardiac and/or respiratory disease.

15. A computer program product stored on a computer readable medium which includes a set of non-transitory computer readable instructions configured to carry out the steps of the method as claimed in claim 14 when said computer program is carried out on the computer.

* * * * *